United States Patent [19]

Watanabe et al.

[11] Patent Number: 4,892,638

[45] Date of Patent: Jan. 9, 1990

[54] INSTRUMENT FOR DETERMINATION OF THE BASE SEQUENCE OF DNA

[75] Inventors: Kenichi Watanabe, Kudamatsu; Tamotu Simada, Akishima; Keiichi Nagai, Higashiyamato; Jirou Tokita; Ryusei Nakano, both of Kokubunji; Tomoaki Sumitani, Hachioji, all of Japan

[73] Assignee: Hitachi, Ltd., Tokyo, Japan

[21] Appl. No.: 116,220

[22] Filed: Nov. 3, 1987

[30] Foreign Application Priority Data

Nov. 4, 1986 [JP] Japan ................................. 61-260740

[51] Int. Cl.$^4$ ....................... G01N 27/28; G01N 27/26
[52] U.S. Cl. ............................. 204/299 R; 204/182.8; 435/287
[58] Field of Search ......................... 204/299 R, 182.8; 435/6, 287; 935/77

[56] References Cited

U.S. PATENT DOCUMENTS

| | | | |
|---|---|---|---|
| 3,801,467 | 4/1974 | Nobe et al. | 165/30 |
| 4,679,615 | 7/1987 | Livre | 165/58 X |
| 4,707,235 | 11/1987 | Englert et al. | 204/182.8 |

FOREIGN PATENT DOCUMENTS

| | | | |
|---|---|---|---|
| 1047563 | 3/1986 | Japan | 435/287 |
| 1047564 | 3/1986 | Japan | 435/287 |
| 1234347 | 10/1986 | Japan | 204/299 R |
| 2182656 | 8/1987 | Japan | 204/299 R |

OTHER PUBLICATIONS

Blasius & Augustin "Hochspannungspapieriono-phoretiche Trennug gemischter Cyamo-thiocyanato-chromate (III) in Temperature-gradienten", Journal of Chromatography, 73 (1972) pp. 298–300.

Blasius & Klemm "Hochspannungspapierionophorese in Temperatur-gradienten und in Nicht wassrigen Losungmitteln", Journal of Chromatography, 108, No. 1, (1975) pp. 323–328.

Primary Examiner—John F. Niebling
Assistant Examiner—John S. Starsiak, Jr.
Attorney, Agent, or Firm—Antonelli, Terry & Wands

[57] ABSTRACT

An instrument for determination of the base sequence of deoxyribonucleic acid (DNA) which is designed to dectect DNA fragments in course of gel electrophoresis in real time to determine the base sequence of DNA, and comprises a gel electrophoretic panel part wherein DNA fragments labeled with a radioisotope are supplied to four places in a gel for four kinds of complementary strand synthesis reaction systems, respectively, and subjected to electrophoresis to form an electrophoretic pattern of the DNA fragments, and a detection part for detecting the electrophoretic pattern of the DNA fragments provided at a predetermined position in said gel electrophoretic panel part so as to have a position resolving power in a direction perpendicular to the direction of electrophoretic migration of the DNA fragments, and which instrument has a means for making the temperature of the gel in the vicinity of the detection part for detecting the electrophoretic pattern of the DNA fragments higher than that on the DNA fragment supply part side. By virtue of the provision of said means, the distance between two adjacent DNA bands similar to each other in molecular weight can be elongated, the resolving power for DNA bands can be improved, and the base sequence of nucleic acid can be determined with high precision.

4 Claims, 7 Drawing Sheets

F I G. 8
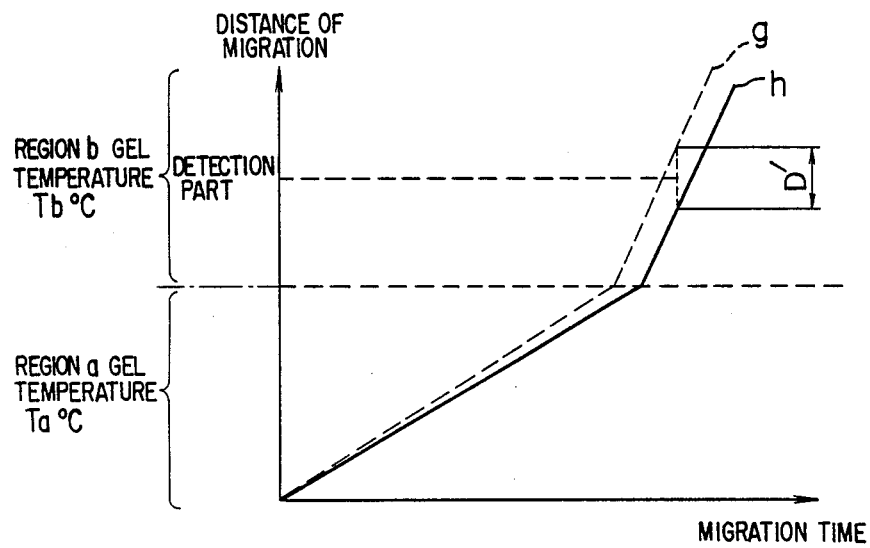

INSTRUMENT FOR DETERMINATION OF THE BASE SEQUENCE OF DNA

BACKGROUND OF THE INVENTION

1. Field of the Invention

This invention relates to an instrument for automatic determination of the base sequence of deoxyribonucleic acid (DNA), particularly to an instrument for determination of the base sequence of DNA which has high resolving power and sensitivity for DNA fragments similar to one another in molecular weight.

2. Related Art Statement

As one example of structure of conventional instrument (a real-time DNA fragment detection type gel electrophoretic instrument) in which DNA fragments in course of gel electrophoresis are detected in real time and the base sequence of DNA is determined thereby, in FIG. 1 is shown the structure of an instrument in which $\beta$-ray radiated from DNA fragments in course of gel electrophoresis are detected in real time and the gel electrophoretic pattern is automatically read. In FIG. 1, gel 8 is placed vertically, being held between an electrophoretic plate 6 and an electrophoretic plate 7. Wells 9 for supplying a DNA sample are provided at the upper end of the gel. A buffer solution tank 1 and a buffer solution tank 3 are attached to the upper part and the lower part, respectively, of the gel 8. A buffer solution 2 and a buffer solution 4 are placed in the buffer solution tank 1 and the buffer solution tank 3, respectively, and are in contact with the upper end and the lower end, respectively, of the gel 8. An electric source power 5 is connected to the buffer solution tank 1 and the buffer solution tank 3 and applied a direct current high voltage so that the upper end of the gel 8 becomes a negative electrode.

When a DNA fragment sample labeled with a radioisotope such as $^{32}P$ or $^{35}S$ is supplied to wells 9 for four kinds of complementary strand synthesis reaction system (A reaction system, C reaction system, G reaction system and T reaction system), respectively, the DNA fragments migrate from the negative electrode towards the positive electrode [F. Sanger et al., "DNA sequencing with chain-terminating inhibitors", Proc. Natl. Acad. Sci. USA, 74, 12, pp. 5463–5467 (1977)]. In this case, the lower the molecular weight of DNA fragment, the higher the migration speed, and DNA fragments having the same molecular weights form a DNA band (a band which DNA fragments having the same molecular weights form on the gel) 10.

In this instrument, slits 13 for detecting $\beta$-ray are provided on the side of the electrophoretic plate 6 or the electrophoretic plate 7, and $\beta$-ray detectors 14 are attached. When the DNA bands pass in front of the slit 13, $\beta$-ray radiated from the DNA band enter the $\beta$-ray detector 14. Outputs from the $\beta$-ray detectors 14 pass through a signal processing circuit 15 and then enter a computer 16. The computer 16 conducts data processing and determines the base sequence. Although one set of the $\beta$-ray detectors 14 are used in this instrument, it is, of course, also possible to use two or more sets.

FIG. 2 is a cross-sectional view showing the structure of the $\beta$-ray detector 14 in detail. A scientillator 23 is attached to the end of a photo-multiplier tube 21 through silicone grease 22, and the whole detector is packed in a housing code 24 for shielding from light. The $\beta$-ray 25 radiated from the DNA band 10 passes through the slit 13 and is converted into light 26 in the scientillator 23.

The light 26 goes out of the scientillator, passes through the silicone grease 22, and enter the photo-multiplier tube 21, in which it is converted into electric current and detected. A film 27 between the slit 13 and the gel 8 serves for the purpose of insulating the slit 13 from the gel 8 electrically and preventing the slit 13 from being contaminated with the radioisotope in the DNA band 10. The film 27 is made of a material which transmits $\beta$-ray (e.g, a polyester film) and has such a thickness as cause no lowering of the detection sensitivity or precision.

In order to elevate the detection sensitivity in a part for detecting $\beta$-ray radiated from DNA band, the slit width should be, as shown in FIG. 3, broadened to increase the amount of $\beta$-ray which enter the $\beta$-ray detector. However, DNA band similar to one another in molecular weight are similar also in distance of migration and overlap in the slit part, resultings in a low resolving power for the DNA bands. On the other band, enhancement of the resolving power for the DNA bands similar in distance of migration by narrowing the slit width leads, as shown in FIG. 4, to a decrease of the amount of $\beta$-ray which enters the $\beta$-ray detector, and hence to a lowering of the sensitivity. Thus, the conventional instruments are disadvantageous.

In prior art, there have been neither disclosed nor considered control of the temperature of a gel through which DNA fragments migrate by electropheresis, for the purpose of enhancing the resolving power and sensitivity for such DNA bands similar in molecular weight.

As described above, in the conventional instruments for determination of the base sequence of DNA, improvement in the resolving power and sensitivity for DNA fragments similar in molecular weight has been neither disclosed nor taken into consideration, and the sensitivity is low in determination of the base sequences of DNA fragments similar in molecular weight. Thus, the conventional instruments have been not sufficiently satisfactory.

SUMMARY OF THE INVENTION

An object of this invention is to provide an instrument for determination of the base sequence of DNA which has high resolving power and sensitivity for DNA fragments similar in molecular weight and permits determination of the base sequence of nucleic acid with high precision.

In a conventional instrument for determination of the base sequence of DNA in which the determination is carried out by separating DNA fragments on a gel by electrophoresis, and then transferring thus obtained electrophoretic pattern to a X-ray film by autoradiography the larger the number of DNA bands each of which is a band formed on the gel by DNA fragments having the same molecular weights, the larger the number of base sequences which can be read at a time. Therefore, it is sufficient that the distance between the adjacent DNA bands is narrow to such an extent that discrimination between these DNA bands is not prevented.

On the other band, in a real-time DNA fragment detection type gel electrophoretic instrument, DNA fragments in course of electrophoresis are detected in real-time by means of a detector attached to a gel electrophoretic plate, whereby the sequence of DNA is determined. Therefore, separation of a large number of DNA bands on a gel at the same time is not necessary, and it is sufficient that the distance between the adjacent DNA bands is wide to such as extent that said distance is suitable for separation between these DNA bands.

Thus, in conventional autoradiography it is necessary to separate DNA fragment on a gel in a wide range. On the other hand, in a real-time DNA fragment detection type gel electrophoretic instrument relating to the present invention, in case that DNA fragments to be detected are long chain, the distance between those fragments is required to be elongated.

The object of this invention described above can be achieved by properly controlling the temperature of a gel through which DNA bands migrate by electrophoresis, in a real-time DNA fragment detection type electrophoretic instrument, and thereby obtaining an electrophoretic pattern in which the distance between two adjacent DNA bands similar to each other in molecular weight is elongated. In detail, the temperature of the gel in the vicinity of DNA band detection parts attached to an electrophoretic plate of the gel electrophoretic instrument is made about 10° C. to about 30° C. higher than the temperature of the gel on the DNA fragment supply part side, whereby the migration speed of DNA bands in the vicinity of the detection parts is increased, so that the distance between two adjacent DNA bands similar in molecular weight can be properly elongated, and there can be obtained a real-time DNA fragment detection type gel electrophoretic instrument which is excellent both in resolving power and in sensitivity.

A first feature of the invention consists in an instrument for determination of the base sequence of DNA which is designed to detect DNA fragment in course of electrophoresis in real time to determine the base sequence of DNA, and comprises a gel electrophoretic panel part wherein DNA fragments labeled with a radioisotope are supplied to a gel and subjected to electrophoresis to form an electrophoretic pattern of the DNA fragments, and a detection part for detecting the electrophoretic pattern of the DNA fragments provided at a predetermined position in said gel electrophoretic panel part, and which instrument has a means for making the temperature of the gel in the vicinity of the detection part for detecting the electrophoretic pattern of the DNA fragments higher than that on the DNA fragment supply part side.

A second feature of the invention consists in an instrument for determination of the base sequence of DNA which is designed to detect DNA fragments in course of electrophoresis in real time to determine the base sequence of DNA, and comprises a gel electrophoretic panel part wherein DNA fragments labeled with a radioisotope are supplied to four places in a gel for four kinds of complementary strand synthesis reaction systems, respectively, and subjected to electrophoresis to form an electrophoretic pattern of the DNA fragments, and a detection part for detecting the electrophoretic pattern of the DNA fragments provided at a predetermined position in said gel electrophoretic panel part so as to have a position resolving power in a direction perpendicular to the direction of electrophoretic migration of the DNA fragments, and which instrument has a means for making the temperature of the gel in the vicinity of the detection part for detecting the electrophoretic pattern of the DNA fragments higher than that on the DNA fragment supply part side.

BRIEF DESCRIPTION OF THE DRAWINGS

FIG. 8 is a graph showing the relationship between migration time and distance of migration of DNA bands in the gel electrophoretic pattern of the instrument of this invention shown in FIG. 6.

DETAILED DESCRIPTION OF THE INVENTION

Figure 1:
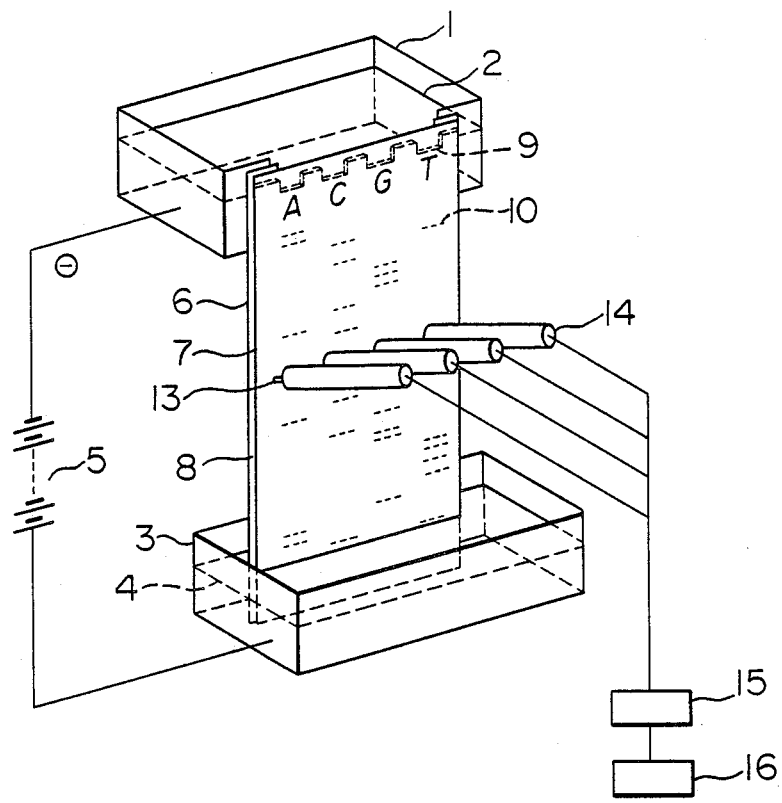
FIG. 1 is a perspective view showing the structure of a conventional real-time DNA fragment detection type gel electrophoretic instrument.
Figure 2:
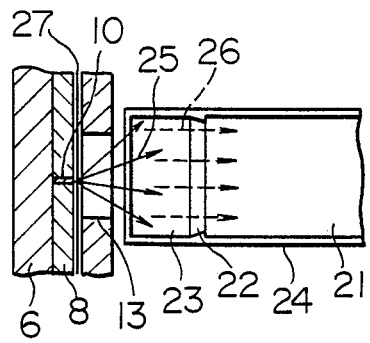
FIG. 2 is a schematic view showing the structure of β-ray detector of the conventional instrument shown in FIG. 1.

In the real-time DNA fragment detection type gel electrophoretic instrument of this invention, it is preferable to make the temperature of the gel in the vicinity of the detection part for detecting an electrophoretic pattern of DNA fragments 10° C. to 30° C. higher than that on the DNA fragment supply part side.

As a means for making the temperature of the gel in the vicinity of the detection part for detecting an electrophoretic pattern of DNA fragments higher than that on the DNA fragment supply part side, it is recommendable to provide a low-temperature thermostat panel on the DNA fragment supply part side, and a high-temperature thermostat panel in the vicinity of the detection part for detecting an electrophoretic pattern of DNA fragments.

It is also possible to provide a thermostat panel of water circulation type using a heat exchanger tube which has the function described below, in a gel electrophoretic panel part between the DNA fragment supply part side and the vicinity of the detection part for detecting an electrophoretic pattern of DNA fragments. This thermostat panel circulates water successively from the DNA fragment supply part side toward the detection part for detecting an electrophoretic pattern of DNA fragments, and thereby makes the temperature of the gel in the vicinity of the detection part for detecting an electrophoretic pattern of DNA fragments higher than that on the DNA fragment supply part side.

When the difference between the temperature of the gel on the DNA fragment supply part side and that in the DNA band detection part is less than 10° C., the effect of elongating the distance between two adjacent DNA bands similar to each other in molecular weight is insufficient, and no sufficient distance for separation of the two adjacent DNA bands can be attained, so that the resolving power of the gel electrophoretic instrument is not sufficiently improved. Therefore, it is not desirable. The larger the above-mentioned temperature difference of the gel, the higher the resolving power. But when it is too large, troubles such as breakage of the electrophoretic plate due to the temperature difference are caused, and usually, the limit of the temperature difference seems to be about 30° C. Although the temperature of gel in conventional instrument is various depending on literatures, it is described, for example, in Mitsuru Takanami and Tatsuo Ohi "Manual of DNA Sequence Analysis" Kodansha Co., Ltd., 1983 that the temperature of gel is usually about 40° C. and is adjusted to about 70° C. when degeneracy phenomenon (compression) is reduced. However, it is not disclosed therein at all that the temperature of gel in the vicinity of a part for detecting an electrophoretic pattern of DNA fragment is made different from that in other parts.

Next, the action of the real-time DNA fragment detection type gel electrophoretic instrument of this invention is explained below in comparison with a conventional instrument with reference to the drawings.

Figure 5:
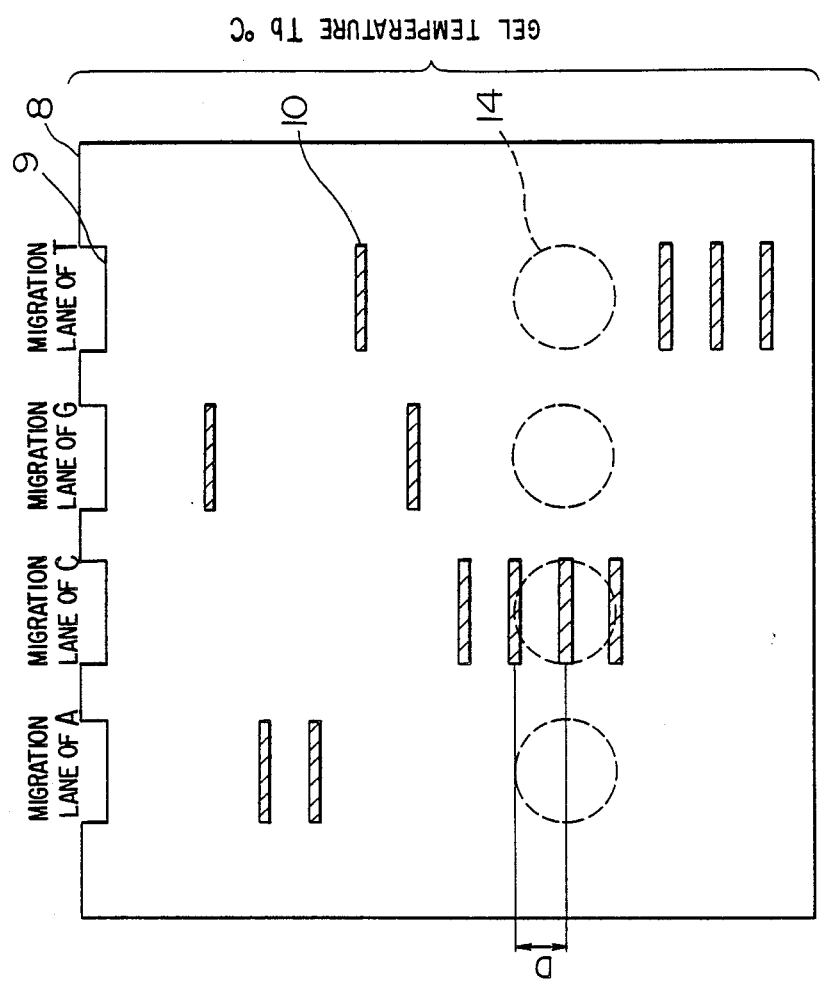
FIG. 5 is an illustration showing the electrophoretic pattern of the conventional instrument shown in FIG. 1.
Figure 6:
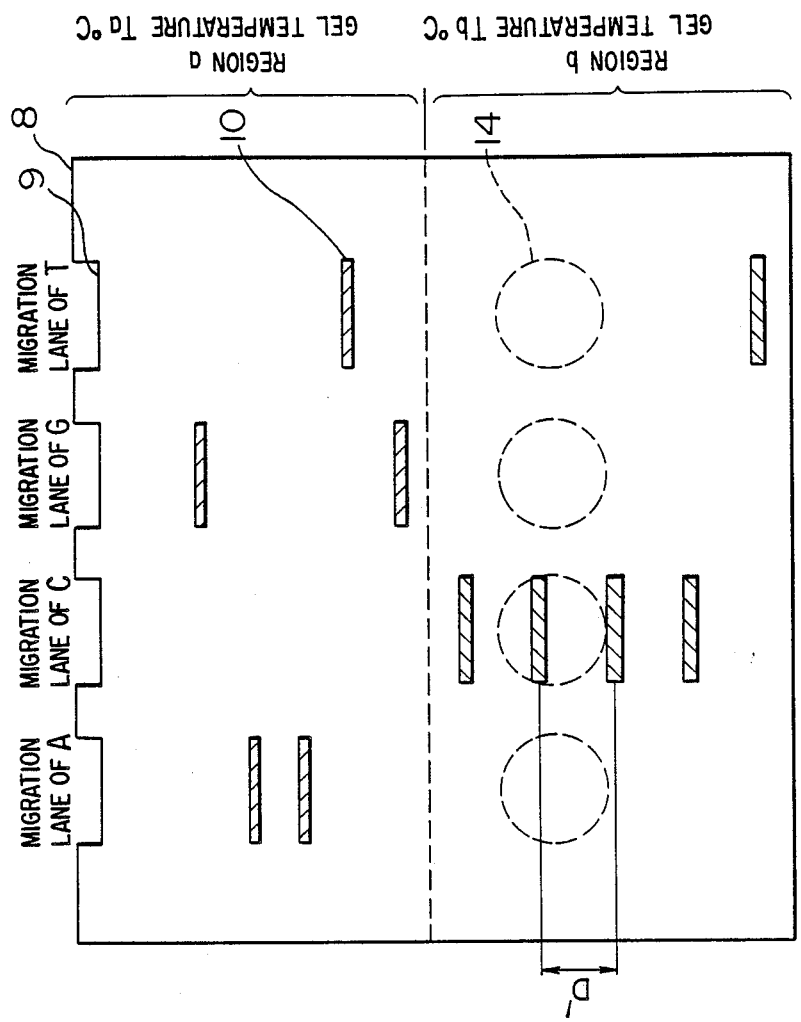
FIG. 6 is an illustration showing a gel electrophoretic pattern of the instrument of this invention shown in FIG. 10.

A gel electrophoretic pattern in a conventional instrument is shown in FIG. 5, and a gel electrophoretic pattern in the instrument of this invention in FIG. 6. In FIG. 5 and FIG. 6, DNA fragments supplied to wells 9 migrate through a gel 8 while forming a DNA band 10 and pass in front of $\beta$-ray detectors 14. D is distance between the adjacent DNA bands 10 in the place of attaching the $\beta$-ray detector 14 in the conventional instrument, and D' is distance between the adjacent DNA bands 10 in the $\beta$-ray detector 14 part in the instrument of this invention. The temperature of gel in the conventional instrument shown in FIG. 5 is substantially uniformly Tb° C (e.g., about 70° C.) throughout the gel. On the other hand, the temperature of gel in the instrument of this invention shown in FIG. 6 is adjusted to Tb° C (e.g., about 70° C.) in the region b of the place of attaching the $\beta$-ray detectors 14 and to Ta° C (e.g., about 40° C.) in the other region a of DNA fragment supply part, and it is controlled so as to satisfy the formula Tb > Ta. Thus, in this invention, the temperature of gel in the place of attaching the $\beta$-ray detector 14 is higher than that in the DNA fragment supply part side, i.e., the side toward the well 9. In practice, the temperature of gel in the region a and the region b shown in FIG. 6 varies gently in the vicinity of the interface of these regions, but in order to give a simplified explanation, it is assumed that the temperature of gel varies rapidly in the interface of the region a and the region b. Changing the temperature of gel stepwise and changing it continuously bring about the same action and effects.

Figure 7:
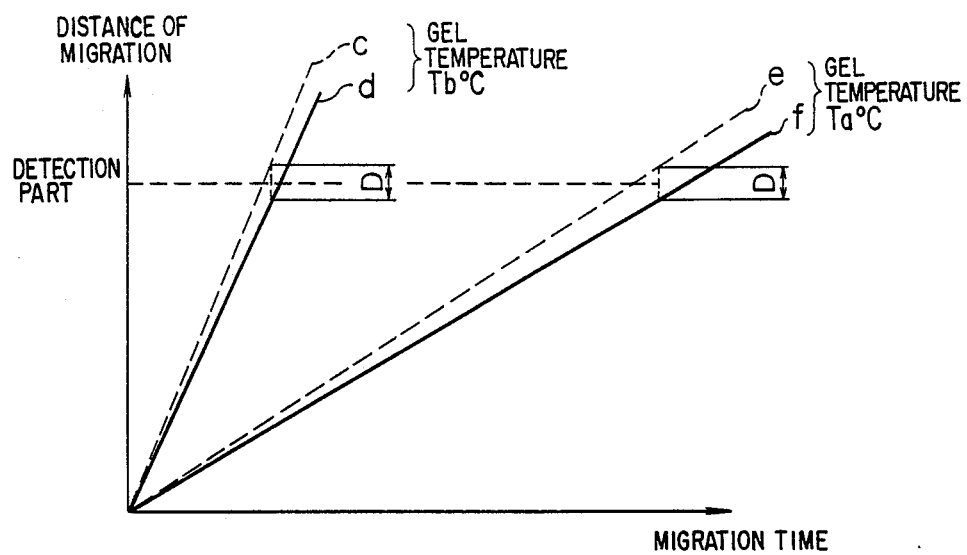
FIG. 7 is a graph showing the relationship between migration time and distance of migration of DNA bands in the gel electrophoretic pattern of the conventional instrument shown in FIG. 5.

FIG. 7 and FIG. 8 shows the relationship between migration time (along the axis of abscissa) and distance of migration (along the axis of ordinate) in the case of the gel used in the conventional instrument or the gel used in the instrument of this invention, respectively. In FIG. 7 and FIG. 8, the broken lines c, e and g and the full lines d, f and h show the distances of migration of DNA fragments having a length of i bases and that of DNA fragments having a length of (i+i) bases, respectively, and D and D' are distances between the adjacent DNA bands at the detection part, respectively. FIGS. 7 and 8 correspond to FIGS. 5 and 6, respectively. The straight lines c and d in FIG. 7 show the distances of migration of DNA fragments in the case of the gel used in the conventional instrument and the temperature of this gel is Tb° C (e.g., about 70° C.). For reference, the distance of migration in the case where the temperature of the gel is Ta° C (e.g., about 40° C.) are shown by the straight lines e and f. The bent lines g (the broken line) and h (the full line) in FIG. 8, which have stepwise changes in slope, show the distances of migration in the case of the gel according to this invention, and the temperature of this gel is Ta° C in the region a or Tb° C in the region b. Here, the distance D' between the adjacent DNA bands can be approximately represented by a product of time difference until the DNA fragments having a length of i bases and those having a length of (i+i) bases arrive at the detection part by the migration speed of the DNA fractions at the detection part, but the bent lines g and h in FIG. 8 have a larger time difference than the straight lines c and d in FIG. 7 and a higher migration speed than the straight lines e and f. Thus, according to this invention, the distance D' between the adjacent DNA bands can be made larger than the distance D between the adjacent DNA bands of the conventional instrument.

Figure 3:
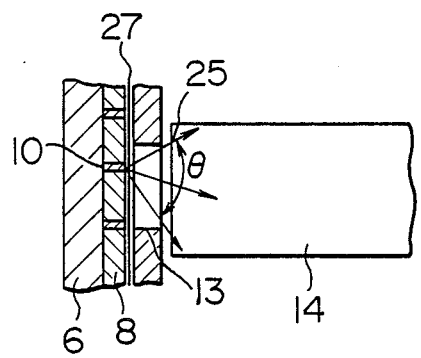
FIG. 3 and FIG. 4 are illustrations showing the action in β-ray detection part of the gel electrophoretic pattern of conventional instrument shown in FIG. 5.
Figure 4:
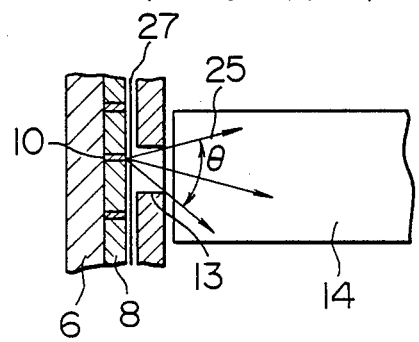
Figure 9:
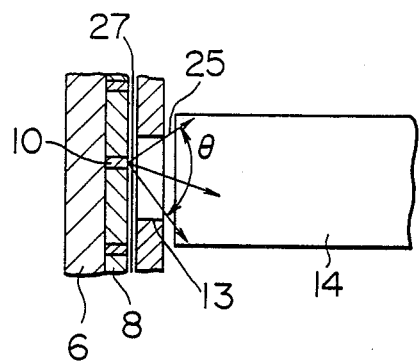
FIG. 9 is an illustration showing the action in β-ray detection part of the gel electrophoretic pattern of the instrument of this invention shown in FIG. 6.

FIG. 3 and FIG. 4 are illustrations showing the action in $\beta$-ray detection part of the conventional instrument which correspond FIG. 5, and FIG. 9 is an illustration showing the action in $\beta$-ray detection part of the instrument of this invention which corresponds FIG. 6. When a DNA band 10 migrates through a gel 8 and passes in front of a slit 13, $\beta$-ray 25 radiated from the DNA band 10 passes through the slit 13 and enters a $\beta$-ray detector 14.

In FIG. 3, two DNA bands 10 similar to each other in molecular weight enter the slit 13 at the same time, and therefore separation of DNA fragments similar in molecular weight is difficult. In FIG. 4, this problem is solved by narrowing the width of the slit 13. But in this case, the angle $\ominus$ at which the $\beta$-ray 25 radiated from the DNA band 10 enters the $\beta$-ray detector after passing through the slit 13 is decreased, so that the amount of the $\beta$-ray 25 which enters the $\beta$-ray detector 14 is decreased. Thus, in the case of the gel used in the conventional instrument, it is difficult to reconcile the resolving power for DNA fragments similar in molecular weight and the amount of the $\beta$-ray which enters the detector.

On the other hand, when the distance between two adjacent DNA bands 10 is elongated by means of the instrument of this invention, it becomes possible, as shown in FIG. 9, to allow only one DNA band 10 at a time to enter the slit 13 without narrowing the width of the slit 13. Therefore, the resolving power for DNA bands 10 similar in molecular weight can be improved without decreasing the amount of the $\beta$-ray which enters the $\beta$-ray detector 14.

As described above in detail, the real-time DNA fragment detection type gel electrophoretic instrument makes it possible to elongate the distance between two adjacent DNA bands at the $\beta$-ray detection part for DNA bands; to improve the resolving power for DNA bands similar to one another in molecular weight without decreasing the amount of $\beta$-ray which enters the $\beta$-ray detector through the slit; and to determine the base sequence of DNA with high precision.

This invention is further explained below in more detail by way of the following Examples with reference to the drawings. In the drawings, parts expressed by the same symbols are the same parts or parts having the same functions.

EXAMPLE 1

Figure 10:
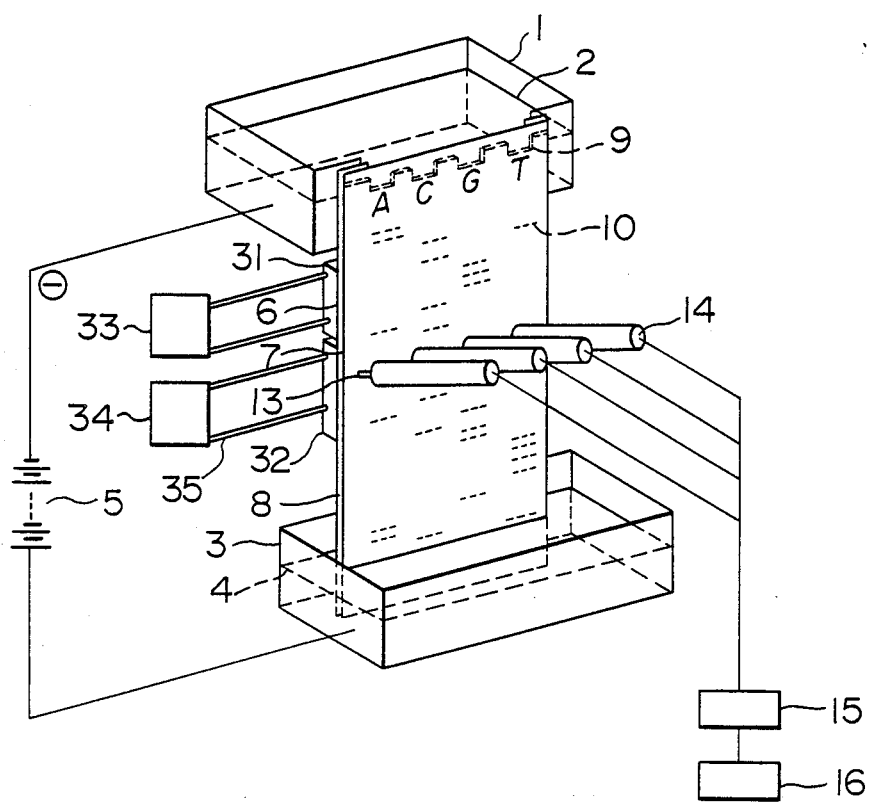
FIG. 10 is a perspective view showing the structure of the real-time DNA fragment detection type gel electrophoretic instrument shown in Example 1.

FIG. 10 is a schematic view showing one example of structure of the real-time DNA fragment detection type gel electrophoretic instrument of this invention. As shown in FIG. 10, in the instrument of this invention, a low-temperature thermostat panel 31 and a high-temperature thermostat panel 32 are attached to the side of a gel electrophoretic plate 6. The place of attaching the high-temperature thermostat panel 32 is near the place of attaching a β-ray detector 14 for DNA bands 10, while the place of attaching the low-temperature thermostat panel 31 is on the DNA fragment supply part side nearer to wells 9 for supplying DNA fragments. The low-temperature thermostat panel 31 and the high-temperature thermostat panel 32 are connected to a low-temperature thermostated water tank 33 and a high-temperature thermostated water tank 34, respectively, through piping 35 which constitute a water jacket.

According to this Example, the temperature (about 50° C. to about 80° C.) of a gel 8 in the place of attaching the β-ray detector 14 for DNA bands 10 becomes higher than the temperature (about 30° C. to about 60° C.) on the well 9 side, so that the distance between two adjacent DNA bands at the detection part is elongated on the working principle described above. Therefore, the resolving power for DNA bands 10 similar in molecular weight can be greatly improved without decreasing the amount of β-ray which enters the β-ray detector 14.

EXAMPLE 2

Figure 11:
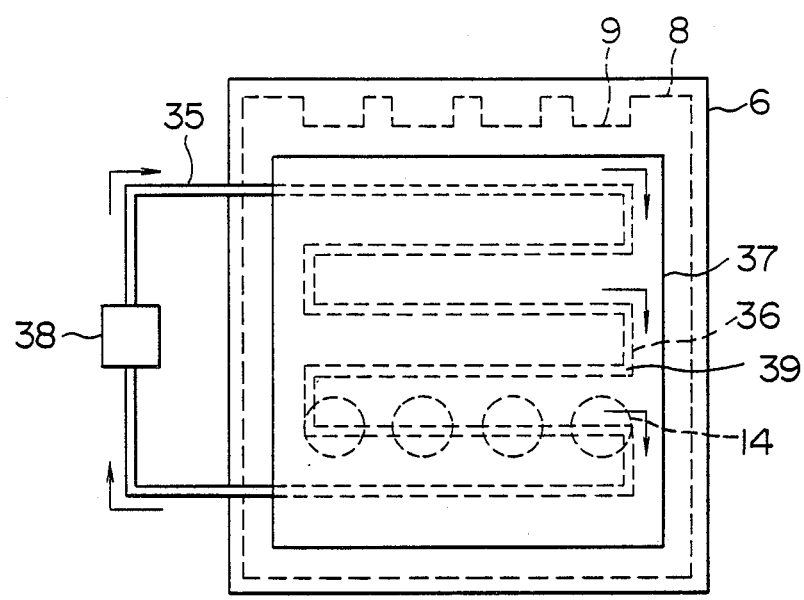
FIG. 11 is a schematic view showing the structure of front of the real-time DNA fragment detection time gel electrophoretic instrument described in Example 2.

FIG. 11 is a schematic view showing another example of structure of the gel electrophoretic instrument of this invention. As shown in FIG. 11, a thermostat panel 37 is attached to a gel electrophoretic plate 6. The thermostat panel 37 is connected to a thermostated water tank 38 through piping 35. A heat exchanger tube 36 runs inside the thermostat panel 37, and circulating water 39 is circulated from the well 9 side toward the place of attaching a β-ray detector 14. In the gel electrophoretic instrument shown in FIG. 11, when the amount of the circulating water 39 is properly controlled, a sufficient cooling effect can be obtained near the wells 9, and in the vicinity of the place of attaching the β-ray detector 14, the temperature of the circulating water 39 rise and therefore the cooling effect can be gradually lessened. In this case, the temperature (about 50° C. to about 80° C.) of a gel 8 in the place of attaching the β-ray detector 14 can be made higher than the temperature (about 30° C. to about 60° C.) of the gel on the well 9 side, so that the distance between two adjacent DNA bands at the detection part can be elongated. Therefore, the resolving power for DNA bands can be improved as in Example 1. While the gel temperature varies stepwise in the structure shown in FIG. 10 of Example 1, it varies continuously in the second structure of Example 2. However, these two structures bring about exactly the same effects.

What is claimed is:

1. An instrument for determination of the base sequence of deoxyribonucleic acid (DNA) which is designed to detect DNA fragments in course of gel electrophoresis in real time to determine the base sequence of DNA, and comprises:

an electrophoretic gel (8), supported between a first and a second plate (7 and 6) and having a well (9) at an upper end thereof to which DNA fragments are to be supplied;

a first buffer solution tank (1) attached to the upper side of said gel which contains a first buffer solution (2) being in contact with the upper end of said gel;

a second buffer solution tank (3) attached to the lower side of said gel which contains a second buffer solution (4) being in contact with an lower end of said gel;

an electric power source (5) connected between said first and second buffer solution tank so that a direct current high voltage is supplied to said gel and the upper end of said gel becomes a negative electrode;

a detector (14) attached to said first plate (7) at a determined position which detects DNA fragments migrating through said gel when the DNA fragments pass in front thereof;

a first thermostat panel (31) attached to said second plate (6) at a first region (a) near said well (9) to which water is supplied at a controlled low temperature; and a second thermostat panel (32) attached to said second plate (6) at a second region (b) near the place where detector (14) is attached to which water is supplied at a controlled temperature higher than said low temperature.

2. An instrument for determination of the base sequence of DNA according to claim 1, wherein a difference between the temperature of said low-temperature water and that of said higher temperature water is in the range of 10° C. to 30° C.

3. An instrument for the determination of the base sequence of deoxyribonucleic acid (DNA) which is designed to detect DNA fragments in course of gel electrophoresis in real time to determine the base sequence of DNA, and comprises:

an electrophoretic gel (8), supported between a first plate (7) and a second plate (6) and having four wells (9) at an upper end thereof to which DNA fragments are to be supplied to four kinds of complimentary strand synthesis reaction systems, respectively, a first buffer solution tank (1) attached to the upper side of said gel which contains a first buffer solution (2) being in contact with the upper end of said gel;

a second buffer solution tank (3) attached to the lower side of said gel which contains a second buffer solution (4) being in contact with an lower end of said gel;

an electric power source (5) connected between said first and second buffer solution tank so that a direct current high voltage is supplied to said gel and the upper end of said gel becomes a negative electrode;

a detector (14) attached to said first plate (7) at a determined position which detects DNA fragments migrating through said gel when the DNA fragments pass in front thereof;

a first thermostat panel (31) attached to said second plate (6) at a first region (a) near said well (9) to which water is supplied at a controlled low temperature; and a second thermostat panel (32) attached to said second plate (6) at a second region (b) near the place where detector (14) is attached to which water is supplied at a controlled temperature higher than said low temperature.

4. An instrument for the determination of the base sequence of DNA according to claim 3, wherein a difference between the temperature of said low-temperature water and that of said higher temperature water is in the range of 10° C. to 30° C.

* * * * *